United States Patent [19]

Iwao et al.

[11] 4,425,333

[45] Jan. 10, 1984

[54] SULFUR-CONTAINING ACYLAMINO ACIDS

[75] Inventors: Jun-ichi Iwao, Takarazuka; Masayuki Oya, Ibaraki; Tadashi Iso, Sakai, all of Japan

[73] Assignee: Santen Pharmaceutical Co., Ltd., Osaka, Japan

[21] Appl. No.: 314,064

[22] PCT Filed: Apr. 2, 1981

[86] PCT No.: PCT/JP81/00074

§ 371 Date: Oct. 19, 1981

§ 102(e) Date: Oct. 19, 1981

[87] PCT Pub. No.: WO81/02893

PCT Pub. Date: Oct. 15, 1981

[30] Foreign Application Priority Data

Apr. 2, 1980 [JP] Japan .................. 55-44358

[51] Int. Cl.³ .............. C07C 103/52; A61K 37/02
[52] U.S. Cl. ................. 424/177; 260/112.5 R; 548/201; 548/533
[58] Field of Search ........... 260/112.5 R; 548/200, 548/537, 538; 424/177

[56] References Cited

U.S. PATENT DOCUMENTS

| | | | |
|---|---|---|---|
| 4,046,889 | 2/1976 | Ondetti et al. | 260/112.5 |
| 4,192,878 | 5/1978 | Ondetti | 260/112.5 |
| 4,248,883 | 2/1981 | Sawayama | 260/112.5 R |
| 4,282,235 | 8/1981 | Ondetti | 260/112.5 R |
| 4,283,328 | 8/1981 | Stammer | 260/112.5 R |

FOREIGN PATENT DOCUMENTS

| | | | |
|---|---|---|---|
| 1978 | 5/1979 | European Pat. Off. | 260/112.5 |
| 7477 | 2/1980 | European Pat. Off. | 260/112.5 |
| 3012140 | 10/1980 | Fed. Rep. of Germany | 260/112.5 |
| 54-66675 | 5/1979 | Japan | 260/112.5 |
| 54-100369 | 8/1979 | Japan . | |
| 54-103867 | 8/1979 | Japan . | |
| 54-154763 | 12/1979 | Japan . | |
| 55-9060 | 1/1980 | Japan . | |
| 55-11547 | 1/1980 | Japan . | |
| 56-49373 | 5/1981 | Japan | 260/112.5 |
| 56-92849 | 7/1981 | Japan | 260/112.5 |
| 2000508 | 1/1979 | United Kingdom | 260/112.5 |
| 2018248 | 10/1979 | United Kingdom | 260/112.5 |

OTHER PUBLICATIONS

145975k "Pharmaceutical Composition Containing a Proline Derivative and a Diuretic" Horovitz et al.; Pharmaceuticals, vol. 91, 1979.

2281-x "Amides of Cyclic Amino Acids" Wiskott, Erik; Chemical Abstracts, vol 92, 1980.

Primary Examiner—Robert Gerstl
Attorney, Agent, or Firm—Frishauf, Holtz, Goodman & Woodward

[57] ABSTRACT

This invention relates to the new thiazolidine and pyrrolidine compounds represented by the following general formula

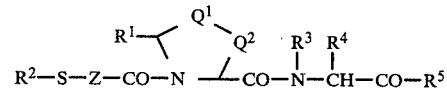

wherein p1 $Q^1$ and $Q^2$ are methylene or sulfur atom;
Z is alkylene containing 1 to 3 carbon atoms;
$R^1$ is hydrogen, alkyl, aryl or heterocycle;
$R^2$ is hydrogen, alkyl, acyl, aryl, heterocycle or mercapto radical;
$R^3$ is hydrogen or alkyl;
$R^4$ is hydrogen, alkyl, aryl, pyrroridine ring formed with $R^3$, or thiazolidine ring formed with $R^3$;
$R^5$ is hydroxy or amino, which may be substituted by alkyl or aryl.

The compounds of this invention are synthesized by the condensation of sulfur-containing acyl thiazolidine carboxylic acid or sulfur-containing acyl pyrrolidine carboxylic acid with amino acid.

The compounds of this invention are useful for antihypertensive agent.

16 Claims, No Drawings

SULFUR-CONTAINING ACYLAMINO ACIDS

This invention relates to sulfur-containing acylamino acids and related salts and antihypertensive compositions containing these compounds as main ingredients, which have the following formula

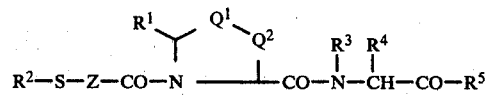 [I]

wherein
- $Q^1$ and $Q^2$ are methylene or sulfur atom, but at least one of them is methylene;
- Z is straight or branched alkylene which contains 1 to 3 carbon atoms;
- $R^1$ is hydrogen, lower alkyl, cycloalkyl, higher alkyl, aralkyl, phenyl, furyl, thienyl, pyridyl or naphthyl, which may be substituted by 1 to 3 groups selected from lower alkyl, hydroxy, $R^2$—S—, lower alkoxy, halogen, nitro, amino, lower alkylamino, lower alkanoylamino, aroylamino, lower alkanoyloxy, aroyloxy, lower alkylenedioxy, carboxy, sulfamoyl, lower alkylaminosulfamoyl or cyano, but when $R^1$ is hydrogen, $Q^1$ and $Q^2$ are not methylene at the same time;
- $R^2$ is hydrogen, lower alkyl, lower alkanoyl, cycloalkanecarbonyl, higher alkanoyl, phenyl-lower alkanoyl, substituted phenyl-lower alkanoyl, benzoyl, substituted benzoyl, pyridylcarbonyl, benzyloxycarbonyl, substituted benzyloxycarbonyl, $R^6$—S—; or the specified $R^1$ groups other than hydrogen;
- $R^3$ is hydrogen or lower alkyl;
- $R^4$ is hydrogen, lower alkyl, phenyl, aralkyl, pyrrolidine ring formed with $R^3$ or thiazolidine ring formed with $R^3$, which may be substituted by hydroxy, lower alkanoyloxy, aroyloxy, aralkyloxy, lower alkoxy, amino, guanidino, carboxy, lower alkoxycarbonyl, phenoxycarbonyl, aralkyloxycarbonyl, carbamoyl, mercapto, lower alkylthio, aralkylthio, lower alkanoylmercapto, aroylmercapto, imidazolyl or indolyl;
- $R^5$ is hydroxy or amino, which may be substituted by lower alkyl, lower alkanoyloxy-lower alkyl, imido-lower alkyl, aralkyl or phenyl;
- $R^6$ is lower alkenyl, higher alkenyl, tetrahydrofurfuryl or the specified $R^1$ groups other than hydrogen;
the same shall be applied hereinafter.

The compounds of this invention are synthesized by such methods as the following A, B and C.

(A) The active derivatives of compounds represented by the formula

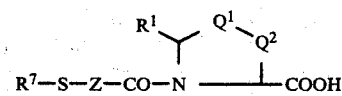 [II]

wherein
$R^7$ is groups excluded hydrogen from the above-mentioned $R^2$;
the same shall be applied hereinafter
and the compounds represented by the formula

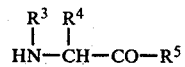 [III]

are condensed by a general method such as mixed anhydride method, etc. in synthesizing peptides to give the compounds of this invention represented by the formula.

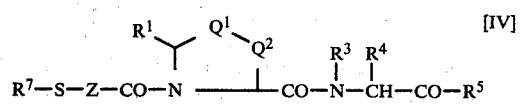 [IV]

The resulting compounds are acidified with hydrochloric acid, trifluoroacetic acid, etc., alkalified with sodium hydroxide, ammonia, etc., or treated by catalytic hydrogenation with palladium-carbon, electrolytic reduction, or reduction with complex metal hydride such as sodium borohydride or with metal to give the compounds of this invention wherein $R^2$ is hydrogen and/or wherein $R^5$ is hydroxy. The diastereoisomers of the products can be separated and purified by a general method such as fractional recrystallization, chromatography, etc.

(B) The compounds represented by the formula

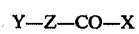 [V]

wherein
X is hydroxy or halogen;
Y is halogen;
the same shall be applied hereinafter
react with the compounds represented by the formula

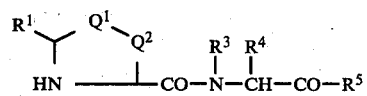 [VI]

by a general method such as Schotten-Baumann reaction, etc. to give the products represented by the formula.

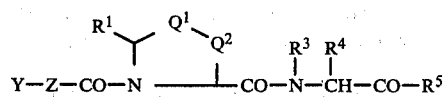 [VII]

The products react with salt of benzylmercaptan, thioacetic acid or thiobenzoic acid such as potassium salt, etc. to give the compounds [IV] of this invention.

(C) The compounds represented by the formula

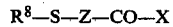 ([VIII]

wherein
$R^8$ is lower alkyl, acyl such as acetyl, pivaloyl, benzoyl, etc., aralkyl such as benzyl, etc., X—CO—Z—S— or $R^6$—S—react with the above-mentioned compounds [VI] by the above method A or B to give the compounds of this invention represented by the formula

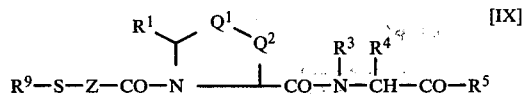

wherein R⁹ is groups excluded hydrogen from the above mentioned R².

The compounds of this invention represented by the formula [II] synthesized by the above mentioned A, B or C can form the conventional salts to be generally used as medicine such as sodium salt, potassium salt, calcium salt, aluminum salt, ammonium salt, diethylamine salt, triethanolamine salt, etc. The compounds [I] of this invention have the stereoisomers because they have one or more asymmetric carbon atoms. These stereoisomers are also within the limit of this invention. Examples are shown below, although this invention is not limited to these ones.

EXAMPLE 1

N-[2R,4R)-[3-(S-Acetyl-3-mercaptopropanoyl)-2-(2-hydroxyphenyl)-4-thiazolidinyl]carbonyl]glycine To the solution of 1.78 g of (2R,4R)-3-(S-acetyl-3-mercaptopropanoyl)-2-(2-hydroxyphenyl)-4-thiazolidinecarboxylic acid dissolved in 30 ml of dry tetrahydrofuran (It is abbreviated to THF hereinafter.) 0.51 g of N-methylmorpholine is added. To the reaction mixture 0.68 g of isobutyl chlorocarbonate is added at a temperature of −15 to −10° C. After stirring it for 30 minutes, the solution of 0.75 g of glycine and 1.0 g of N-methylmorpholine dissolved in 5 ml of THF and 20 ml of water is added to it. After stirring it for 1 hour while being back to the room temperature gradually, and then removing THF in vacuo, the residue is acidified with N—HCl, and extracted with ethyl acetate. The organic layer is washed with saturated aqueous sodium chloride solution, dried over anhydrous magnesium sulfate, and concentrated in vacuo. The residue is purified by silica gel column chromatography to give 1.44 g (70%) of the titled compound.

mp 98°–99° C. (ethyl acetate-n-hexane).
$[\alpha]_D^{25}+126.4°$ (c=1.1, methanol).
IR (nujol, cm⁻¹, to be applied hereinafter unless specified) 3340, 1740, 1690, 1670, 1640, 1465, 1250, 1215, 775, 730.

EXAMPLE 2

(2S)-N-[(2R,4R)-[3-(S-Acetyl-3-mercaptopropanoyl)-2-(2-hydroxyphenyl)-4-thiazolidinyl]carbonyl]phenylalanine To the solution of 3.55 g of (2R,4R)-3-(S-acetyl-3-mercaptopropanoyl)-2-(2-hydroxyphenyl)-4-thiazolidinecarboxylic acid dissolved in the 60 ml of THF 1.0 g of N-methylmorpholine is added. To the reaction mixture 1.4 g of isobutyl chlorocarbonate is added at a temperature of −15° to −10° C. The suspension obtained by stirring it for 1 hour is added to 60 ml of the aqueous solution of 3.38 g of L-phenylalanine and 2.0 g of triethylamine with stirring under ice-cooling. After stirring it under ice-cooling for 10 minutes and at room temperature for an additional 10 minutes, the solution is concentrated in vacuo. The concentrate is washed with two 100-ml portions of ether, acidified with conc. hydrochloric acid, and extracted with ethyl acetate. The organic layer is washed with saturated aqueous sodium chloride solution, dried over anhydrous magnesium sulfate, and concentrated in vacuo to give 4.8 g (96%) of the titled compound.

mp 91°–95° C. (amorphous powder).
$[\alpha]_D^{28}+151.2°$ (c=0.9, methanol).
IR 3280, 3130, 1728, 1680, 1655, 1625, 1600, 760.

EXAMPLE 3

(2S)-N-[(2R,4R)-[3-(S-Acetyl-3-mercaptopropanoyl)-2-(2-hydroxyphenyl)-4-thiazolidinyl]carbonyl]tryptophan The suspension of mixed anhydride is prepared by using 1.78 g of (2R,4R)-3-(S-acetyl-3-mercaptopropanoyl)-2-(2-hydroxyphenyl)-4-thiazolidinecarboxylic acid, 0.51 g of N-methylmorpholine and 0.68 g of isobutyl chlorocarbonate in the same manner as Example 1. To the suspension 20 ml of the aqueous solution of 2.04 g of L-tryptophan and 1.0 g of triethylamine are added. The mixture is stirred under ice-cooling for 30 minutes and at room temperature for an additional 30 minutes, and concentrated in vacuo. The concentrate is washed with ether, acidified with N—HCl, and filtered. The precipitate is washed well with dilute hydrochloric acid and water to give 1.7 g (63%) of the titled compound.

mp 105°–115° C. (amorphous powder).
$[\alpha]_D^{28}+143.4°$ (c=0.5, methanol).
IR 3295, 1730, 1655, 1525, 1230, 1130, 960, 750.

EXAMPLE 4

(2S)-N-[(2R,4R)-[3-(S-Acetyl-3-mercaptopropanoyl)-2-(2-hydroxyphenyl)-4-thiazolidinyl]carbonyl]glutamic acid The suspension of mixed anhydride in THF is prepared by using 1.78 g of (2R,4R)-3-(S-acetyl-3-mercaptopropanoyl)-2-(2-hydroxyphenyl)-4-thiazolidinecarboxylic acid, 0.51 g of N-methylmorpholine and 0.68 g of isobutyl chlorocarbonate. The suspension is added to the aqueous solution of 1.5 g of L-glutamic acid and 2.0 g of triethylamine, and treated in the same manner as Example 2 to give 1.9 g (80%) of the titled compound.

mp 93°–98° C. (amorphous powder).
$[\alpha]_D^{28}+129.3°$ (c=1.0, methanol).
IR 3280, 1720, 1690, 1653, 1623, 1600, 762.

EXAMPLE 5

(2S)-N-[(2R,4R)-[3-(S-Acetyl-3-mercaptopropanoyl)-2-(2-hydroxyphenyl)-4-thiazolidinyl]carbonyl]serine The suspension of mixed anhydride is prepared by using 3.55 g of (2R,4R)-3-(S-acetyl-3-mercaptopropanoyl)-2-(2-hydroxyphenyl)-4-thiazolidinecarboxylic acid, 1.0 g of N-methylmorpholine, 1.4 g of isobutyl chlorocarbonate and 60 ml of THF in the same manner as Example 1. To the suspension 20 ml of the aqueous solution of 2.1 g of L-serine and 2.0 g of triethylamine is added. The mixture is stirred under ice-cooling for 30 minutes and at room temperature for an additional 1 hour. After removing THF in vacuo, it is acidified with N—HCl, and extracted with ethyl acetate. The organic layer is washed with saturated aqueous sodium chloride solution, dried over anhydrous magnesium sulfate, and concentrated in vacuo. The residue is crystallized from benzene to give 3.6 g (82%) of the titled compound.

mp 175.5°–177.0° C. (dec.) (ethanol-ether).
$[\alpha]_D^{32}+174.0°$ (c=0.5, methanol).
IR 3280, 1700, 1685, 1625, 1590, 1210. 755.

EXAMPLE 6

(2S)-N-[(2R,4R)-[3-(S-Acetyl-3-mercaptopropanoyl)-2-(2-hydroxyphenyl)-4-thiazolidinyl]carbonyl]leucine The suspension of mixed anhydride in THF is prepared by using 1.78 g of (2R,4R)-3-(S-acetyl-3-mercaptopropanoyl)-2-(2-hydroxyphenyl)-4-thiazolidinecarboxylic acid, 0.51 g of N-methylmorpholine and 0.68 g of isobutyl chlorocarbonate. To the suspension the aqueous solution of 1.31 g of L-leucine and 1.0 g of triethylamine is added, and treated in the same manner as Example 1 to give 1.8 g (77%) of the titled compound.

mp 78°-84° C. (amorphous powder).
$[\alpha]_D^{32} + 115.2°$ (c=0.75, methanol).
IR 3220, 1720, 1650, 1620, 1230, 1130, 760.

EXAMPLE 7

(2S)-N-[(2R,4R)-[3-(S-Acetyl-3-mercaptopropanoyl)-2-(2-hydroxyphenyl)-4-thiazolidinyl]carbonyl]methionine The suspension of mixed anhydride in THF is prepared by using 5.3 g of (2R,4R)-3-(S-acetyl-3-mercaptopropanoyl)-2-(2-hydroxyphenyl)-4-thiazolidinecarboxylic acid, 1.5 g of N-methylmorpholine and 2.0 g of isobutyl chlorocarbonate. To the suspension the aqueous solution of 4.5 g of L-methionine and 3.0 g of N-methylmorpholine is added, and treated in the same manner as Example 1 to give 1.6 g (66%) of the titled compound.

mp 59°-64° C. (amorphous powder).
$[\alpha]_D^{30} + 150.3°$ (c=0.8, methanol).
IR 3340, 1735, 1725, 1650, 1615, 1600, 755.

EXAMPLE 8

(2S)-N-[(2R,4R)-[3-(S-Acetyl-3-mercaptopropanoyl)-2-(2-hydroxyphenyl)-4-thiazolidinyl]carbonyl]tyrosine The suspension of mixed anhydride in THF is prepared by using 3.55 g of (2R,4R)-3-(S-acetyl-3-mercaptopropanoyl)-2-(2-hydroxphenyl)-4-thiazolidinecarboxylic acid, 1.0 g of N-methylmorpholine and 1.4 g of isobutyl chlorocarbonate. To the suspension 40 ml of N-NaOH solution of 3.6 g of L-tryrosine is added, and treated in the same manner as Example 1 to give 4.8 g (93%) of the titled compound.

mp 95°-96.5° C.
$[\alpha]_D^{28} + 141.8°$ (c=1.1, methanol).
IR 3240, 1730, 1690, 1660, 1630, 1225, 767, 726.

EXAMPLE 9

(2S)-N-[(2R,4R)-[3-(S-Acetyl-3-mercaptopropanoyl)-2-(2- hydroxyphenyl)-4-thiazolidinyl]carbonyl]proline The suspension of mixed anhydride in THF is prepared by using 1.78 g of (2R,4R)-3-(S-acetyl-3-mercaptopropanoyl)-2-(2-hydroxyphenyl)-4-thiazolidinecarboxylic acid, 0.51 g of N-methylmorpholine and 0.68 g of isobutyl chlorocarbonate. To the suspension the solution of 1.0 g of L-proline and 1.0 g of triethylamine dissolved in aqueous THF is added, and treated in the same manner as Example 1 to give 1.5 g (68%) of the titled compound.

mp 186-187° C. (ethyl acetate).
$[\alpha]_D^{28} + 122.3°$ (c=0.5, methanol).
IR 3295, 1750, 1685, 1635, 1600, 1235, 1170, 935, 760.

EXAMPLE 10

N-[(2R,4R)-[3-(S-Benzoyl-3-mercaptopropanoyl)-2-(2-hydroxyphenyl)-4-thiazolidinyl]carbonyl]glycine ethyl ester To the solution of 2.09 g of (2R,4R)-3-(S-benzoyl-3-mercaptopropanoyl)-2-(2-hydroxyphenyl)-4-thiazolidinecarboxylic acid dissolved in 30 ml of dry THF, 0.51 g of N-methylmorpholine is added. To the mixture 0.68 g of isobutyl chlorocarbonate is added at a temperature of $-15°$ to $-10°$ C. After stirring it for 15 minutes, the solution of 0.7 g of glycine ethyl ester hydrochloride and 0.51 g of N-methylmorpholine dissolved in 5 ml of THF and 15 ml of water is added to it. After stirring it for 1 hour while being back to the room temperature gradually, and then removing THF in vacuo, the mixture is extracted with ethyl acetate. The organic layer is washed with N—HCl, water, saturated aqueous sodium chloride solution, in order, dried over anhydrous magnesium sulfate, and concentrated in vacuo. The residue is crystallized from ethyl acetate-benzene to give 2.43 g (82%) of the titled compound.

mp 134°-135° C. (ethyl acetate).
$[\alpha]_D^{25} + 95.4°$ (c=1.1, methanol).
IR 3270, 3060, 1749, 1690, 1655, 1630, 1456, 1203, 1042, 909, 788, 764, 723.

EXAMPLE 11

N-[(2R,4R)-[3-(S-Acetyl-3-mercaptopropanoyl)-2-(2-hydroxyphenyl)-4-thiazolidinyl]carbonyl]glycine ethyl ester The suspension is prepared by using 1.78 g of (2R,4R)-3-(S-acetyl-3-mercaptopropanoyl)-2-(2-hydroxyphenyl)-4-thiazolidinecarboxylic acid, 0.51 g of N-methylmorpholine and 0.68 g of isobutyl chlorocarbonate. To the suspension the solution of 0.7 g of glycine ethyl ester hydrochloride and 0.51 g of N-methylmorpholine dissolved in aqueous THF is added, and treated in the same manner as Example 10 to give 1.8 g (82%) of the titled compound.

mp 130°-131° C. (ethyl acetate-n-hexane).
$[\alpha]_D^{25} + 119.0°$ C. (c=0.9, methanol).
IR 3270, 3050, 1729, 1676, 1650 (shoulder), 1635, 1545, 1460, 1290, 1225, 760, 730.

EXAMPLE 12

(2S)-N$^2$-[(2R,4R)-[3-(S-Acetyl-3-mercaptopropanoyl)-2-(2-hydroxyphenyl)-4-thiazolidinyl]carbonyl]histidine methyl ester The suspension of mixed anhydride is prepared by using 1.78 g of (2R,4R)-3-(S-acetyl-3-mercaptopropanoyl)-2-(2-hydroxyphenyl)-4-thiazolidinecarboxylic acid, 0.51 g of N-methylmorpholine, 0.68 g of isobutyl chlorocarbonate and 30 ml of dry THF in the same manner as Example 1. To the suspension the solution of 1.21 g of L-histidine methyl ester dihydrochloride and 1.0 g of triethylamine dissolved in 10 ml of aqueous THF is added. After stirring it under ice-cooling for 30 minutes and at room temperature for an additional 30 minutes, and then removing THF in vacuo, the separated oil is obtained by decantation, and crystallized from aqueous sodium bicarbonate solution and benzene to give 1.4 g (55%) of the titled compound.

mp 122°-125° C. (acetone-cyclohexane).
$[\alpha]_D^{28} + 167.8°$ (c=0.5, methanol).

IR 3365, 3235, 1735, 1675, 1630, 1605, 1205, 1135, 945, 765.

EXAMPLE 13

(2S)-N-[(2R,4R)-[3-(S-Acetyl-3-mercaptopropanoyl)-2-(2-hydroxyphenyl)-4-thiazolidinyl]carbonyl]phenylalanine t-butyl ester The suspension of mixed anhydride is prepared by using 1.78 g of (2R,4R)-3-(S-acetyl-3-mercaptopropanoyl)-2-(2-hydroxyphenyl)-4-thiazolidinecarboxylic acid, 0.51 g of N-methylmorpholine, 0.68 g of isobutyl chlorocarbonate and 30 ml of dry THF in the same manner as Example 1. To the suspension the solution of 1.29 g of L-phenylalanine t-butyl ester hydrochloride and 0.51 g of N-methylmorpholine dissolved in 5 ml of THF and 10 ml of water is added. The mixture is stirred at room temperature for 1 hour, and then concentrated in vacuo. To the residue 50 ml of water is added. The mixture is extracted with ethyl acetate. The organic layer is washed with saturated aqueous sodium bicarbonate solution, dried over anhydrous magnesium sulfate, and concentrated in vacuo. The residue is crystallized from n-hexane to give 2.02 g (72%) of the titled compound.

mp 140°–142° C. (ethyl acetate-n-hexane).
$[\alpha]_D^{24}+126.1°$ (c=1.3, methanol).
IR 3360, 3260, 1700, 1680, 1625, 1580, 1295, 1271, 1245, 1235, 1222, 1150, 1026.

EXAMPLE 14

(2S)-N-[(2R,4R)-[3-(S-Acetyl-3-mercaptopropanoyl)-2-(2-hydroxyphenyl)-4-thiazolidinyl]carbonyl]alanine t-butyl ester The suspension of mixed anhydride in THF is prepared by using 1.78 g of (2R,4R)-3-(S-acetyl-3-mercaptopropanol)-2-(2-hydroxyphenyl)-4-thiazolidinecarboxylic acid and 0.51 g of N-methylmorpholine and 0.68 g of isobutyl chlorocarbonate. To the suspension the solution of 0.9 g of L-alanine t-butyl ester hydrochloride and 0.51 g of N-methylmorpholine dissolved in dry THF is added, and treated in the same manner as Example 13. Thus obtained oil is purified by silica gel column chromatography to give 1.6 g (66%) of the titled compound.

mp 170°–171.5° C. (dec.) (ethyl acetate-benzene).
$[\alpha]_D^{32}+98.7°$ (c=0.5, methanol).
IR 3360, 1700, 1685, 1595, 1450, 1130, 1050, 750.

EXAMPLE 15

(2S)-N-[[1-(S-Benzoyl-3-mercaptopropanoyl)-5-(2-hydroxyphenyl)-2-pyrrolidinyl]carbonyl]phenylalanine t-butyl ester To the solution of 1.43 g of 1-(S-benzoyl-3-mercaptopropanoyl)-5-(2-hydroxyphenyl)-2-pyrrolidinecarboxylic acid (mp 89°–92° C. (dec.); $[\alpha]_D^{25}+47.4°$ (c=1.0, methanol)) and 0.3 g of N-methylmorpholine dissolved in 30 ml of dry THF 0.41 g of isobutyl chlorocarbonate is added at a temperature of −15° to −10° C. After stirring it for 30 minutes, the solution of 0.77 g of L-phenylalanine t-butyl ester hydrochloride and 0.3 g of triethylamine dissolved in 10 ml of aqueous THF is added to it. After stirring the mixture under ice-cooling for 30 minutes and at room temperature for an additional 30 minutes, and then removing THF in vacuo, the mixture is extracted with ethyl acetate. The organic layer is washed with saturated aqueous sodium bicarbonate solution, water and saturated aqueous sodium chloride solution, in order, dried over anhydrous magnesium sulfate, and concentrated in vacuo. The residue is purified by silica gel column chromatography to give 1.5 g (83%) of the titled compound.

$[\alpha]_D^{28}+20.5°$ (c=0.5, methanol).
IR (neat) 3275, 1730, 1660, 1625, 1600, 1525, 1205, 1155, 1035, 910, 845, 760.

EXAMPLE 16

(2S)-N-[(2R,4R)-[3-(S-Acetyl-3-mercaptopropanoyl)-2-(2-hydroxyphenyl)-4-thiazolidinyl]carbonyl]-o-t-butyltyrosine t-butyl ester The suspension of mixed anhydride in THF is prepared by using 1.78 g of (2R,4R)-3-(S-acetyl-3-mercaptopropanoyl)-2-(2-hydroxyphenyl)-4-thiazolidinecarboxylic acid, 0.51 g of N-methylmorpholine and 0.68 g of isobutyl chlorocarbonate. To the suspension the solution of 1.47 g of o-t-butyltyrosine t-butyl ester dissolved in dry THF is added, and the mixture is treated in the same manner as Example 13. The resulting residue is crystallized from ethyl acetate to give 2.65 g (74%) of the titled compound.

mp 108°–109° C. (ethyl acetate).
$[\alpha]_D^{25}+97.3°$ (c=0.9, methanol).
IR 3320, 3260, 1740, 1725, 1699, 1663, 1630, 1440, 1384, 1265, 1220, 770, 735.

EXAMPLE 17

(2S)-N-[(2R,4R)-[3-(S-Benzoyl-3-mercaptopropanoyl)-2-(2-hydroxyphenyl)-4-thiazolidinyl]carbonyl]phenylalanine To the suspension of 2.09 g of (2R,4R)-3-(S-benzoyl-3-mercaptopropanoyl)-2-(2-hydroxyphenyl)-4-thiazolidinecarboxylic acid, 0.51 g of N-methylmorpholine and 0.68 g of isobutyl chlorocarbonate in THF, the solution of 1.65 g of L-phenylalanine and 1.0 g of triethylamine is added, and the mixture is treated in the same manner as Example 10. The resulting residue is purified by silica gel column chromatography to give 2.0 g (71%) of the titled compound.

mp 95°–100° C. (amorphous powder).
$[\alpha]_D^{30}+131.3°$ (c=1.0, methanol).
IR 3260, 3120, 1730, 1720, 1650, 1630, 1600, 1200, 910, 755.

EXAMPLE 18

(2S)-N-[(2R,4R)-[2-(2-Hydroxyphenyl)-3-(3-mercaptopropanol)-4-thiazolidinyl]carbonyl]phenylalanine In 2 ml of 28% ammonia water 0.5 g of (2S)-N-[(2R,4R)-[3-(S-acetyl-3-mercaptopropanoyl)-2-(2-hydroxyphenyl)-4-thiazolidinyl]carbonyl]phenylalanine is dissolved. The solution is stirred at room temperature for 1 hour, and acidified with hydrochloric acid. The separated crystals are collected by filtration to give 0.4 g (87%) of the titled compound.

mp 95°–101° C. (amorphous powder).
$[\alpha]_D^{28}+150.4°$ (c=0.9, methanol).
IR 3280, 3120, 1722, 1658, 1620, 1600, 762.

EXAMPLE 19

(2S)-N-[(2R,4R)-[2-(2-Hydroxyphenyl)-3-(3-mercaptopropanoyl)-4-thiazolidinyl]carbonyl]serine In 10 ml of 28% ammonia water 0.5 g of (2S)-N-[(2R,4R)-[3-(S-acetyl-3-mercaptopropanoyl)-2-(2-hydroxyphenyl)-4-thiazolidinyl]carbonyl]serine is dissolved. The solution is stirred at room temperature for 30 minutes, and acidified with hydrochloric acid after removing excess ammonia. The separated oil is extracted with ethyl acetate. The organic layer is washed with saturated aqueous sodium chloride solution, dried over anhydrous magnesium sulfate, and ethyl acetate is removed to give 0.4 g (88%) of the titled compound.

mp 140.5°–145° C. (ethyl acetate-benzene).
$[\alpha]_D^{32} +151.4°$ (c=0.5, methanol).
IR 3320, 1685, 1620, 1510, 1230, 1060, 760.

EXAMPLE 20

(2S)-N-[[1-(S-Benzoyl-3-mercaptopropanoyl)-5-(2-hydroxyphenyl)-2-pyrrolidinyl]carbonyl]phenylalanine The mixture of 0.7 g of (2S)-N-[[1-(S-benzoyl-3-mercaptopropanoyl)-5-(2-hydroxyphenyl)-2-pyrrolidinyl]-carbonyl]-phenylalanine t-butyl ester obtained in Example 15, 2.7 g of trifluoroacetic acid and 0.6 g of anisole is stirred at room temperature for 4 hours. After removing trifluoroacetic acid and anisole from it, the reaction mixture is purified by silica gel column chromatography to give 0.5 g (79%) of the titled compound.

mp 72°–102° C. (amorphous powder).
$[\alpha]_D^{28} -41.7°$ (c=0.5, methanol).
IR 3295, 1735, 1655, 1600, 1525, 1205, 1040, 910, 760.

EXAMPLE 21

(2R,2′R,4R,4′R)-3,3′-[3,3′-Dithiobis(propanoyl)]bis]4-[[(1S)-1-carboxy-2-hydroxy]ethylcarbamoyl]-2-(2-hydroxyphenyl)-thiazolidine]

(i) To the solution of 1.56 g of (2R,2′R, 4R, 4′R)-3,3′-[3,3′-dithiobis(propanoyl)]bis[2-(2-hydroxpyhenyl)-4-thiazolidinecarboxylic acid] and 0.51 g of N-methylmorpholine dissolved in 30 ml of dry THF, 0.68 g of isobutyl chlorocarbonate is added at the temperature of −15° to −10° C. The mixture is stirred for 1 hour, and the solution of 1.05 g of L-serine and 1.0 g of triethylamine dissolved in 10 ml of water is added to it. The mixture is stirred under ice-cooling for 30 minutes and at room temperature for an additional 1 hour. After removing THF in vacuo, it is acidified with N-HCl, and extracted with ethyl acetate. The organic layer is washed with saturated aqueous sodium chloride solution, dried over anhydrous magnesium sulfate, and concentrated in vacuo to give 1.4 g (70%) of the titled compound.

mp 128.5°–134.0° C. (dec.).
$[\alpha]_D^{32} +116.6°$ (c=0.5, methanol).
IR 3280, 1730, 1665, 1630, 1460, 1240.

(ii) To the solution of 0.2 g of (2S)-N-[(2R,4R)-2-(2-hydroxyphenyl)-3-(3-mercaptopropanoyl)-4-thiazolidinyl]-carbonyl]serine (TLC: Rf value[a] 0.67) dissolved in 5 ml of methanol 5 ml of 0.1N KI$_3$ is added dropwise. The mixture is stirred for 10 minutes, and then methanol is removed in vacuo. The separated crystals are collected by filtration to give 0.18 g (90%) of the titled compound.

TLC: Rf value[a] 0.42.

(a) Silica gel, chloroform-ethanol-acetic acid (5:5:1).

EXAMPLE 22

(2R,2′R,4R,4′R)-3,3′-[3,3′-Dithiobis(propanoyl)]bis[4-[[(1S)-1-carboxy-2-phenyl]ethylcarbamoyl]-2-(2-hydroxyphenyl)thiazolidine]

(i) To the suspension of 1.56 g of (2R,2′R,4R,4′R)-3,3′-[3,3′-dithiobis(propanoyl)]bis[2-(2-hydroxyphenyl)-4-thiazolidinecarboxylic acid], 0.51 g of N-methylmorpholine and 0.68 g of isobutyl chlorocarbonate in THF the aqueous solution of 1.69 g of L-phenylalanine and 1.0 g of triethylamine is added. The mixture is treated in the same manner as Example 21 (i) to give 1.3 g (72%) of the titled compound.

mp 136°–139° C.
$[\alpha]_D^{28} +139.4°$ (c=0.5, methanol).
IR 3290, 1728, 1660, 1625, 1600, 760.

(ii) By substituting 0.46 g of (2S)-N-[(2R,4R)-[2-(2-hydroxyphenyl)-3-(3-mercaptopropanoyl)-4-thiazolidinyl]carbonyl]phenylalanine )TLC: Rf value[b] 0.44) in the procedure of Example 21 (ii), 0.43 g (93%) of the titled compound is obtained.

TLC: Rf value[b] 0.28.

(b) Silica gel, ethyl acetate-chloroform-acetic acid (10:5:3).

The following compounds are obtained in the same manner as the above examples.

- (2R)-N-[(2R,4R)-[3-(S-Acetyl-3-mercapto-propanoyl)-2-(2-hydroxyphenyl)-4-thiazolidinyl]-carbonyl]-S-benzylcysteine
- (2S)-N-[(2R,4R)-[3-[(2S)-S-Acetyl-3-mercapto-2-methylpropanoyl]-2-(2-hydroxyphenyl)-4-thiazolidinyl]carbonyl]-phenylalanine
- (2S)-N-[(2R,4R)-[3-(S-Pivaloyl-3-mercapto-propanoyl)-2-phenyl-4-thiazolidinyl]carbonyl]aspartic acid
- (2S)-N$^6$-Acetyl-N$^2$-[(4R)-[3-(S-propanoyl-3-mercaptopropanoyl)-2-(4-methoxyphenyl)-4-thiazolidinyl]carbonyl]lysine
- (2S)-N-[(4R)-[3-(S-(4-Methylbenzoyl)-3-mercapto-propanoyl]-2-(3,4-methylenedioxyphenyl)-4-thiazolidinyl]carbonyl]valine
- (2S)-N-[(4R)- [3-[(2S)-S-Benzoyl-3-mercapto-2-methyl-propanoyl]-2- (4-pyridyl)-4-thiazolidinyl]carbonyl]phenyl-alanine
- (2S)-N-[(4R)- [3- [(2S)-S-Benzoyl-3-mercapto-2-methyl-propanoyl]-2-(2-hydroxy-3-methoxy-phenyl)-4-thiazolidinyl]-carbonyl]phenylalanine
- (2R)-S-Acetyl-N- [4) -[(3S)-S-acetyl-2-mercapto-propanoyl]-2-(2-thienyl)-4-thiazolidinyl]carbonyl]-cysteine
- (2S)-N-[(2R,4R)-[2-(2-hydroxyphenyl)-3-[3-[(tetrahydrofurfuryl)disulfanyl]propanoyl]-4-thiazolidinyl]-carbonyl]-phenylalanine
- (2S)-N- [(2R,4R)-[2-(2-Hydroxyphenyl)-3-[3-(aryl) disulfanylpropanoyl]-4-thiazolidinyl]carbonyl]-phenylalanine
- (2S)-N-[(4R)-[2-(4-Hydroxyphenyl)-3-[S-(3-pyridyl)-mercaptoacetyl]-4thiazolidinyl]carbonyl]isoleucine It is clear that the compounds inhibiting angiotensin converting enzyme, which converts the biologically inactive decapeptide, angiotensin I to the active octapeptide, angiotensin II, may be antihypertensive drugs. Thus they were evaluated pharmacologically as an antihypertensive agent by measuring the inhibitory activity against the above enzyme.

PHARMACOLOGICAL TEST 1

As the methods of measurement of angiotensin-converting enzyme activity, the bioassay for the contractile response of isolated smooth muscle or the pressor response of normal animals and the biochemical assay for the enzyme isolated from lung or other organs of animals are known. The former is found more advantageous than the latter for the examination of the convertion of angiotensin I to angiotensin II in vivo. In this present study, therefore, we adopted the bioassay for contractile response of isolated guinea-pig ileum to angiotensin I.

MEASUREMENT OF INHIBITORY ACTIVITY OF ANGIOTENSIN-CONVERTING ENZYME

Isolated guinea-pig ileum was prepared according to a general method. It was suspended in the organ bath containing 20 ml of Throde's solution of 30° C. gassed with 95% $O_2$+5% $CO_2$. The contraction induced by the addition of angiotensin I (final concentration 0.1 μg/ml) at intervals of 10 minutes was recorded on a recticorder (Nihon Koden) for 90 seconds using FD pick up (ST-1T-H, Nihon Koden).

The test compounds were added to the both 5 minutes before the addition of angiotensin I.

The inhibitory activity of angiotensin-converting enzyme was calculated by the following formula.

$$\frac{A-B}{A} \times 100$$

A: the contractile intensity by angiotensin I before the addition of compound.
B: the contractile intensity by angiotensin I after the addition of compound.

From the fact that kininase II, which resolves bradykinin contracting isolated guinea-pig ileum, is identical with angiotensin-converting enzyme, the augmentation of contractile response to brandykinin by test compounds was examined by using bradykinin (0.005 μg/ml) in place of angiotensin I according to the above method. Consequently, the compounds of this invention obtained in Examples inhibited the contractile response to angiotensin I, and enhanced it to bradykinin.

PHAMRMACOLOGICAL TEST 2

The activity of angiotensin-converting enzyme was measured by spectrophotometry according to the method of Biochem. Pharmacol., 20, 1637 (1971). That is, the absorbance of hippuric acid was measured, which is liberated by incubating hippuryl-L-histidyl-L-leucine (HHL) as the substrate in the presence of angiotensin-converting enzyme extracted from rabbit lung.

MEASURMENT OF INHIBITORY ACTIVITY OF ANGIOTENSIN-CONVERTING ENZYME

The reaction mixture is as follows:
100 mM phophate buffer (pH 8.3)
300 mM sodium chloride
5 mM HHL
$10^{-3}$ to $10^{-9}$ M enzyme inhibitor
5 mU enzyme 0.25 ml of the above mixture was incubated at 37° C. for 30 minutes, and the reaction was stopped by adding 0.25 ml of 1N hydrochloric acid. To this solution 1.5 ml of ethyl acetate was added in order to extract hippuric acid. 1.0 ml of ethyl acetate layer was evaporated to dryness, and the obtained residue was dissolved in 1.0 ml of water. The absorbance of this solution was measured at 228 nm.

The inhibitory activity of angiotensin-converting enzyme was calculated by the following formula.

$$\text{Percent inhibition} = \frac{A-B}{A} \times 100$$

A: the absorbance of reaction solution.

B: the absorbance of reaction solution after the addition of compound.

Concentration of compound producing 50% inhibition of angiotensin-converting enzyme ($IC_{50}$)

The solution containing compound at the concentration of $1 \times 10^{-3}$M to $1 \times 10^{-9}$M was incubated, and the present inhibition at each concentration was calculated according to the above formula. And then $IC_{50}$, the concentration of compound producing 50% inhibition of the enzyme activity, was determined. By the examination, the compounds of this invention were proved to inhibit angiotensin-converting enzyme as well as the known mercaptoacylamino acids.

PHARMACOLOGICAL TEST 3

Because recently it is clear that the compounds inhibiting angiotensin I-converting enzyme may be curative of not only renal hypertension but also essential hypertension, the compounds of this invention are estimated as an antihypertensive agent by the following nethod.

METHOD

Male Wistar strain rats weighing 200–300 g were used. Under ether anesthesia, polyethylene cannulae are inserted into carotid artery and jugular vein. The cannula to carotid artery is connected to an electric transducer, while the cannula to jugular vein is connected to an apparatus for continuous infusion. After the complete recovery from anesthesia, angiotensin I is infused intravenously in a dose of 300 ng/kg by the apparatus for continuous infusion, and the pressor response is recorded by polygraph (Nihon Koden, RM-150). The compounds of this invention suspended in 0.5% tragacanth solution are administered orally in a dose of 0.3 ml per 100 g of body weight, and the pressor response to angiotensin I infused intravenously is measured with time.

RESULTS

The compounds of this invention as well as the known antihypertensive mercaptoacylamino acids suppress the pressor response to angiotensin I by administering them orally to unanesthesized rats.

As exercised actually in using antihypertensive agents as the case may be, the compounds of this invention can be also given with the combination of diuretics. The compounds can be administered either orally or parenterally. The dosage forms are tablet, capsule, granule, powder, suppository, injection, etc. In the treatment of hypertension, these preparations can contain not only general excipients but also other antihypertensive agents such as reserpine, α-methyldopa, guanethidine, clonidine, hydralazine, etc. The dose is adjusted depending on symptoms, dosage form, etc., but usual daily dosage is 1 to 5000 mg, preferably 10 to 1000 mg, in one or a few divided doses.

The followings show the examples of formulation.

(1) Oral drug

| (a) tablets | |
|---|---|
| compound of Example 2 | 30 mg |
| lactose | 150 mg |
| crystalline cellulose | 50 mg |
| calcium carboxymethylcellulose | 7 mg |
| magnesium stearate | 3 mg |
| Total | 240 mg |
| compound of Example 5 | 150 mg |

-continued

| (a) tablets | |
|---|---|
| lactose | 60 mg |
| crystalline cellulose | 30 mg |
| calcium carboxymethylcellulose | 7 mg |
| magnesium stearate | 3 mg |
| Total | 250 mg |

The tablets may be treated with common film-coating and further with sugar-coating.

| (b) granule | |
|---|---|
| compound of Example 20 | 30 mg |
| polyvinylpyrrolidone | 25 mg |
| lactose | 385 mg |
| hydroxypropylcellulose | 50 mg |
| talc | 10 mg |
| Total | 500 mg |
| (c) powder | |
| compound of Example 9 | 30 mg |
| lactose | 500 mg |
| starch | 440 mg |
| colloidal silica | 30 mg |
| Total | 1000 mg |
| compound of Example 8 | 300 mg |
| lactose | 230 mg |
| starch | 440 mg |
| colloidal silica | 30 mg |
| Total | 1000 mg |
| (d) capsule | |
| compound of Example 4 | 30 mg |
| lactose | 102 mg |
| crystalline cellulose | 56 mg |
| colloidal silica | 2 mg |
| Total | 190 mg |
| compound of Example 18 | 30 mg |
| glycerin | 349.98 mg |
| butyl p-hydroxybenzoate | 0.02 mg |
| Total | 380 mg |

(2) Injection 1 to 30 mg of compound of Example 1 is contained in 1 ml of the aqueous solution (pH 6.5–7.0).

What we claim is:

1. A compound of the formula (I)

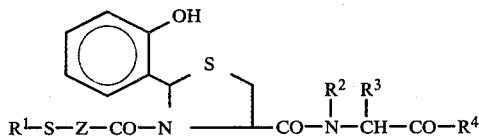

wherein $R_1$ is hydrogen, lower alkanoyl, benzoyl or

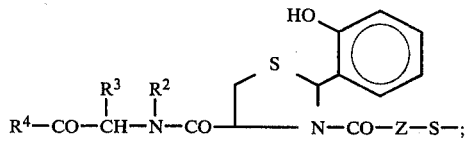

$R^2$ is hydrogen;

$R^3$ is selected from the group consisting of hydrogen, lower alkyl, phenyl, phenyl-lower alkyl, or phenyl or phenyl-lower alkyl substituted by hydroxy, lower alkoxy, amino carboxy, carbamoyl, mercapto, lower alkylthio, lower-alkanoyl-mercapto, imidazoyl or indolyl;

$R^2$ and $R^3$ may be joined to form a pyrrolidine ring;

$R^4$ is a hydroxy or lower alkoxy;

Z is straight or branched alkylene having 1 to 3 carbon atoms; and pharmaceutically acceptable salts of said compound.

2. The compounds and salts of claim 1, wherein Z is —CH$_2$—CH$_2$—.

3. The compound of claim 1, wherein $R^2$ is selected from the group consisting of hydrogen, acetyl and benzoyl.

4. N-[(2R,4R)-[3-(S-Acethyl-3-mercaptopropanoyl)-2-(2-hydroxyphenyl)-4-thiazolidinyl]carbonyl]glycine of the compounds of claim 1.

5. (2S)-N-[(2R,4R)-[3-(S-Acethyl-3-mercaptopropanoyl)-2-(2-hydroxyphenyl)-4-thiazolidinyl]carbonyl]phenylalanine of the compounds of claim 1.

6. (2S)-N-[(2R,4R)-[3-(S-Acetyl-3-mercaptopropanoyl)-2-(2-hydroxyphenyl)-4-thiazolidinyl]carbonyl]tryptophan of the compounds of claim 1.

7. (2S)-N-[(2R,4R)-[3-(S-Acetyl-3-mercaptopropanoyl)-2-(2-hydroxyphenyl)-4-thiazolidinyl]carbonyl]glutamic acid of the compounds of claim 1.

8. (2S)-N-[(2R,4R)-[3-(S-Acetyl-3-mercaptopropanoyl)-2-(2-hydroxyphenyl)-4-thiazolidinyl]carbonyl]leucine of the compounds of claim 1.

9. (2S)-N-[(2R,4R)-[3-(S-Acetyl-3-mercaptopropanoyl)-2-(2-hydroxyphenyl)-4-thiazolidinyl]carbonyl]methionine of the compounds of claim 1.

10. N-[(2R,4R)-[3-S-Benzoyl-3-mercaptopropanoyl)-2-(2-hydroxyphenyl)-4-thiazolidinyl]carbonyl]glycine ethyl ester of the compounds of claim 1.

11. (2S)-N-[(2R,4R)-[3-(S-Benzoyl-3-mercaptopropanoyl)-2-(2-hydroxyphenyl)-4-thiazolidinyl]carbonyl]phenylalanine of the compounds of claim 1.

12. (2S)-N-[(2R,4R)-[2-(2-Hydroxyphenyl)3-(3-mercaptopropanoyl)-4-thiazolidinyl]carbonyl]phenylalanine of the compounds of claim 1.

13. The compounds and salts of claim 3 wherein 2 is —CH$_2$CH$_2$—.

14. A pharmaceutical composition comprising the compound of claim 1 in an amount effective to reduce blood pressure and a pharmaceutically acceptable excipient.

15. A method of reducing blood pressure in a warm blooded animal comprising administering to said warm blooded animal the composition of claim 14.

16. (2S)-N-[(1-(S-Benzoyl-3-mercaptopropanoyl)-5-(2-hydroxyphenyl)-2-pyrrolidinyl]carbonyl]phenylalanine.

* * * * *

UNITED STATES PATENT AND TRADEMARK OFFICE
CERTIFICATE OF CORRECTION

PATENT NO. : 4,425,333

DATED : January 10, 1984

INVENTOR(S) : Jun-ichi IWAO et al

It is certified that error appears in the above-identified patent and that said Letters Patent is hereby corrected as shown below:

Title Page, under "FOREIGN PATENT DOCUMENTS" insert
 --5522673  2/18/80  Japan--.

Title Page, in the ABSTRACT, first line below formula,
 delete "pl".

Column 12, line 20: replace "nethod" with --method--.

Column 14, line 13 (Claim 1): after "amino" insert -- , --.

*Signed and Sealed this*

*Twenty-sixth* Day of *February 1985*

[SEAL]

*Attest:*

DONALD J. QUIGG

*Attesting Officer*   *Acting Commissioner of Patents and Trademarks*